(12) United States Patent
Seo et al.

(10) Patent No.: US 6,313,327 B1
(45) Date of Patent: Nov. 6, 2001

(54) CARBOXYLIC ACID DERIVATIVES AND THEIR SYNTHESIS METHOD

(75) Inventors: Dong Seoul Seo, Shinsung-dong; Joo Hyeon Park, Jeonmin-dong; Jae Young Kim; Seong Ju Kim, both of Shinsung-dong, all of (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/425,961

(22) Filed: Oct. 25, 1999

(30) Foreign Application Priority Data

Jul. 9, 1999 (KR) .................................. 99-27670

(51) Int. Cl.$^7$ ....................................... C07J 9/00
(52) U.S. Cl. .................... 552/553; 552/555; 552/502; 560/116; 560/117; 560/118; 560/120; 560/129
(58) Field of Search .................... 560/129, 117, 560/118, 116, 120; 552/555, 553, 502

(56) References Cited

PUBLICATIONS

Schaap, Formation of stable bicyclic 1,2–Dioxetanes from the addition of single oxygen to p–dioxene and 1,3–dioxole, May 1971, Tetrahedron Letters, and pp. 11757–60.*

"Limits To Etch Resistance For 193–nm Single–Layer Resists" by R.R. Kunz e al., Proc. SPIE 2724, pp. 365–376 (1996).

"Recent Advances in 193 nm Single–Layer Photoresists Based on Alternating Copolymers of Cycloolefins" by F.M. Houlihan et al., Proc. SPIE 3049, pp. 84–91 (1997).

* cited by examiner

*Primary Examiner*—Gary Geist
*Assistant Examiner*—Taylor V. Oh
(74) *Attorney, Agent, or Firm*—Birch, Stewart, Kolasch & Birch, LLP

(57) ABSTRACT

This invention relates to novel carboxylic acid derivatives represented by the following formula I and their synthesis:

Formula I

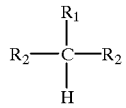

wherein, $R_1$ is an hydrogen atom, an alkyl group or an alkoxy group of 1 to 20 carbon atoms in a linear, branched or cyclic form; $R_2$ is a carboxy group of 1 to 40 carbon atoms in a linear, branched or cyclic form which is unsubstituted, or substituted into a hydroxy group, an ester group and an ether group.

The novel carboxylic acid derivatives are more easily decomposed by acid than t-butyl ester compounds but are not dissolved in basic aqueous solution. According to this invention, carboxylic acid is under condensation with halogen compounds designed to prepare a larger monomolecular compound compared to the conventional method. Further, the condensed site is easily decomposed by acid but is extremely insoluble by basic aqueous solution. The carboxylic acid derivatives in a photoresist composition function not only as a dissolution promoter in the exposed area due to formation of the carboxylic acid, thus enhancement of etching resistance and pattern profile in a resist.

5 Claims, No Drawings

CARBOXYLIC ACID DERIVATIVES AND THEIR SYNTHESIS METHOD

BACKGROUND OF THE INVENTION

1. Field of the Invention

This invention relates to carboxylic acid derivatives and their synthesis method and more particularly, to novel carboxylic acid derivatives represented by the following formula I via introduction of some protecting group which can be easily decomposed by acid, including their synthesis method.

Formula I

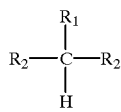

wherein, $R_1$ is an hydrogen atom, an alkyl group or an alkoxy group of 1 to 20 carbon atoms in a linear, branched or cyclic form; $R_2$ is a carboxy group of 1 to 40 carbon atoms in a linear, branched or cyclic form which is unsubstituted, or substituted into a hydroxy group, an ester group and an ether group.

2. Description of the Related Art

As an additive or active ingredient of a resist, an electronic material, carboxylic acid compounds serve to improve the etching resistance and pattern profile of the resist.

It has been reported that one example of such carboxylic acid derivatives introducing t-butyl group as a protecting group includes t-butyl deoxycholate or t-butyl lithocholate (*Proc. SPIE* 3049, 84, 1997).

However, the resist containing such carboxylic acid derivatives has recognized some disadvantages in that the insolubility of basic aqueous solution in a unexposed area cannot be overcome and the resist cannot be easily decomposed by acid.

In consequence, when the resist is developed for the final patterning using developer, the unexposed resist area is etched and this may lead to a poor pattern profile.

SUMMARY OF THE INVENTION

Therefore, an object of this invention is to provide novel carboxylic acid derivatives which have excellent combination of properties such as an easier decomposition by acid than the conventional t-butyl ester compounds including better insolubility in basic aqueous solution, so as to improve the etching resistance and pattern profile in a resist.

Another object of this invention is to provide a method for synthesizing the carboxylic acid derivatives.

To achieve the aforementioned objective, the carboxylic acid derivatives of this invention is characterized by the following formula I.

Formula I

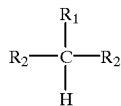

wherein, $R_1$ is an hydrogen atom, an alkyl group or an alkoxy group of 1 to 20 carbon atoms in a linear, branched or cylic form; $R_2$ is a carboxy group of 1 to 40 carbon atoms in a linear, branched or cyclic form which is unsubstituted, or substituted into a hydroxy group, an ester group and an ether group.

Further, this invention is characterized by a method of synthesizing the carboxylic acid derivatives represented by the formula I via reaction between a halogen compound represented by the following formula II and a carboxylic acid compound represented by the following formula III in the presence of a basic catalyst.

Formula II

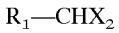
$R_1$—$CHX_2$

Wherein, $R_1$ is the same as defined above; X is F, Cl, Br or I.

Formula III

$R_2$—H

Wherein, $R_2$ is the same as defined above.

DETAILED DESCRIPTION OF THE INVENTION

The carboxylic acid derivatives of this invention is synthesized via one-step reaction between a halogen compound represented by the compound II and a carboxylic acid compound represented by the formula III which are dissolved in an appropriate solvent and stirred with the slow addition of the basic catalyst.

Hence, the examples of the basic catalyst includes any of the general primary, secondary or tertiary amines, pyridines, organic metals or metals. However, in consideration of the fact that the base catalyst should contain a small amount of metal impurities as an electronic material, it is preferred that amine derivatives as organic basic catalyst is employed instead of metal catalysts. The method for synthesizing the carboxylic acid derivatives of this invention can be represented by the following scheme 1:

Scheme 1

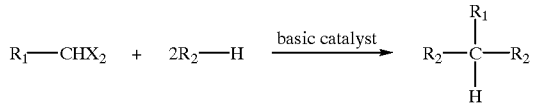

Wherein, $R_1$, $R_2$ and X are the same as defined above.

According to this invention, the halogen compound represented by the formula II is 1,1-dihaloalkane or 1,1-dihaloalkyl alkyl ether, as defined above. The detailed examples of the halogen compound include dibromomethane, 1,1-dibromopropane, 1,1-dichloromethyl methyl ether and 1,1-dichloromethyl 2-norbornyl ether; among them, the reactability of 1,1-dibromopropane is somewhat poor than other halogen compounds.

From the carboxylic acid represented by the formula III of this invention, a majority of the aforementioned functional groups do not affect the reaction process. The detailed examples of functional group in the carboxylic acid include a hydroxy group, ester group, ether group, amide group, epoxy group, amino group, halogen group, lactone group, anhydride group and sulfide group. One or more of the functional groups in the carboxylic acid does not affect the reaction.

Reaction is generally performed at −80 to 150° C. If the reaction temperature is extremely low, the starting materials are not well stirred. By contrast, if the reaction temperature is extremely high, some by-products may be generated.

Meantime, it is preferred that the reaction is performed for 0.5 to 15 hours.

It is preferred that 1.5 to 3.0 equivalents of the carboxylic acid represented by the formula III is employed to the halogen compound represented by the formula II, more preferably in the range of 1.8 to 2.2 equivalents.

In case of synthesizing the carboxylic acid derivatives using the halogen compound, the reaction solvents includes dichloromethane, chloroform, carbon tetrachloride. Acetonitrile, ethylacetate, ethylether, dioxane, dimethyl formamide, dimethyl acetamide, ethanol, methanol, isopropanol or acetone, among them, it is preferred that dichloromethane and dimethyl formamide are employed. Hence, if any solvent can dissolve the halogen compound represented by the formula II and carboxylic acid represented by the formula III or can be dissolved in the reaction mixture without dissolving these starting materials, there are no special restriction in using the solvent.

Based on the carboxylic acid derivatives, so synthesized by the above mentioned, a photoresist composition can be prepared using a basic resin, photo-acid generator, and some additive. Hence, the carboxylic acid derivatives serves to improve various properties such as etching resistance, adhesiveness, pattern profile, resolution and exposure energy.

From the newly synthesized carboxylic acid derivatives of this invention, the reaction mechanism of deoxycholic acid derivatives decomposed by strong acid is shown in the following scheme 2.

lamine (19.4 g), the reaction mixture was stirred at the same temperature for 1 hour and further stirred for 2 hours at room temperature. After the reaction was completed, the reaction mixture was diluted with ethyl acetate, washed with excess of distilled water three times, washed again with a potassium carbonate solution and distilled water. After separating the organic layer, the solution was dried over magnesium sulfate and filtered off. With the complete removal of solvent contained in the remaining solution under vacuum distillation. 25 g of the following compound (I) was obtained.

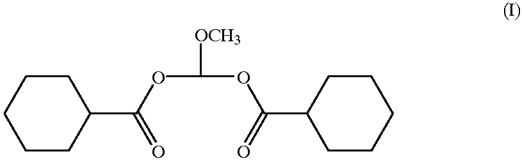

(I)

Scheme 2

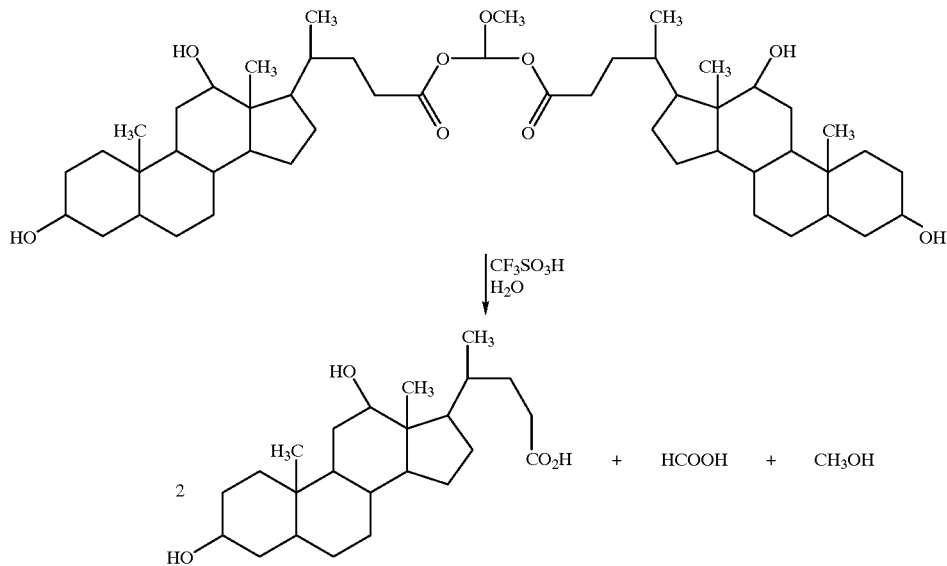

From the above scheme 2, the deoxycholic acid derivatives has an extremely low solubility to basic aqueous solution but the deoxycholic acid generated form the acid-decomposition has an extremely high solubility to basic aqueous solution.

Under the above principle, the deoxycholic acid derivative in a chemical-amplified resist function not only as a dissolution inhibitor on basic aqueous solution in the unexposed area but also as a dissolution promoter on basic aqueous solution in the exposed area due to formation of the deoxycholic acid.

This invention is explained based on the following examples but is not confined to these examples.

EXAMPLE 1

α,α-dichloromethyl methylether (10 g) was slowly added to cyclohexane carboxylic acid (22.3 g) dissolved in dimethyl acetamide at 0° C. With the slow addition of triethy-

EXAMPLE 2

Carboxylic acid derivative was prepared in the same manner as Example 1 using 4-tert-butylcyclohexane carboxylic acid(32.1 g) instead of cyclohexane carboxylic acid (22.3 g), thus obtaining 32 g of the following compound (II).

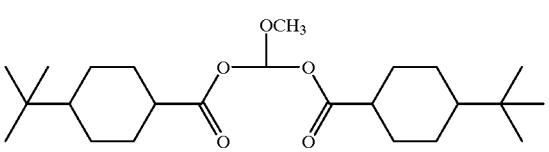

(II)

EXAMPLE 3

Carboxylic acid derivative was prepared in the same manner as Example 1 using norbornane carboxylic acid (24.4 g) instead of cyclohexane carboxylic acid (22.3 g), thus obtaining 26 g of the following compound (III).

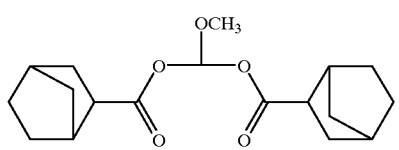

(III)

EXAMPLE 4

Carboxylic acid derivative was prepared in the same manner as Example 1 using norbornene carboxylic acid (24.0 g) instead of cyclohexane carboxylic acid (22.3 g), thus obtaining 24 g of the following compound (IV).

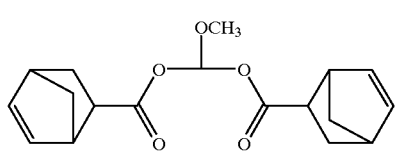

(IV)

EXAMPLE 5

Carboxylic acid derivative was prepared in the same manner as Example 1 using norbornane acetic acid (26.8 g) instead of cyclohexane carboxylic acid (22.3 g), thus obtaining 27 g of the following compound (V).

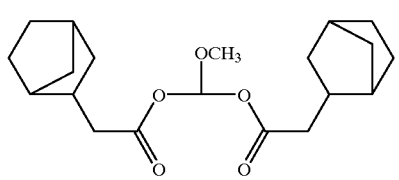

(V)

EXAMPLE 6

Carboxylic acid derivative was prepared in the same manner as Example 1 using 1-adamantane carboxylic acid (31.4 g) instead of cyclohexane carboxylic acid (22.3 g), thus obtaining 28 g of the following compound (VI).

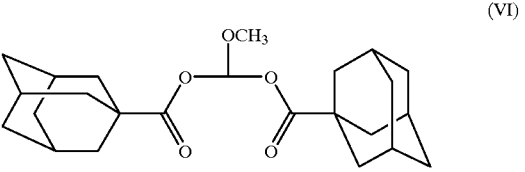

(VI)

EXAMPLE 7

Carboxylic acid derivative was prepared in the same manner as Example 1 using 1-adamantane acetic acid (33.8 g) instead of cyclohexane carboxylic acid (22.3 g), thus obtaining 31 g of the following compound (VII).

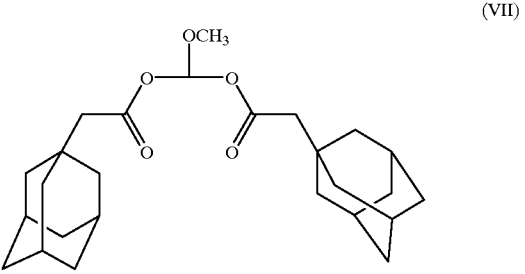

(VII)

EXAMPLE 8

Carboxylic acid derivative was prepared in the same manner as Example 1 using lithocholic acid (65.5 g) instead of cyclohexane carboxylic acid (22.3 g), thus obtaining 59 g of the following compound (VIII).

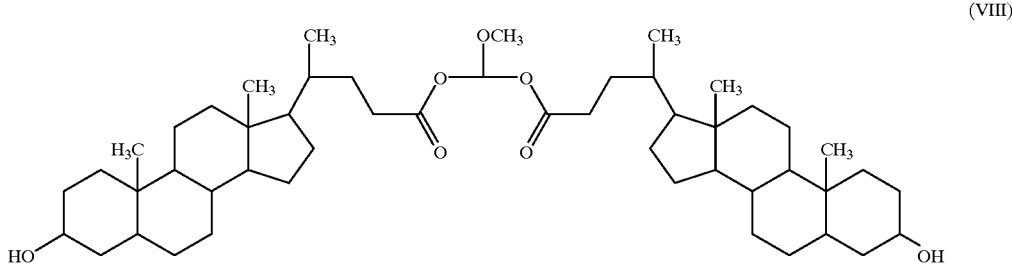

(VIII)

EXAMPLE 9

Carboxylic acid derivative was prepared in the same manner as Example 1 using deoxycholic acid (68.3 g) instead of cyclohexane carboxylic acid (22.3 g), thus obtaining 60 g of the following compound (IX).

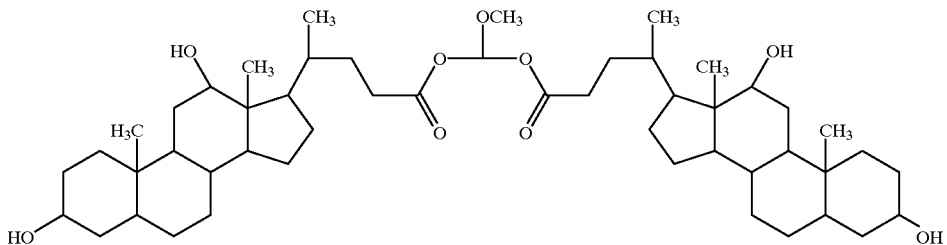

(IX)

EXAMPLE 10

Carboxylic acid derivative was prepared in the same manner as Example 1 using hyodeoxycholic acid (68.3 g) instead of cyclohexane carboxylic acid (22.3 g), thus obtaining 63 g of the following compound (X).

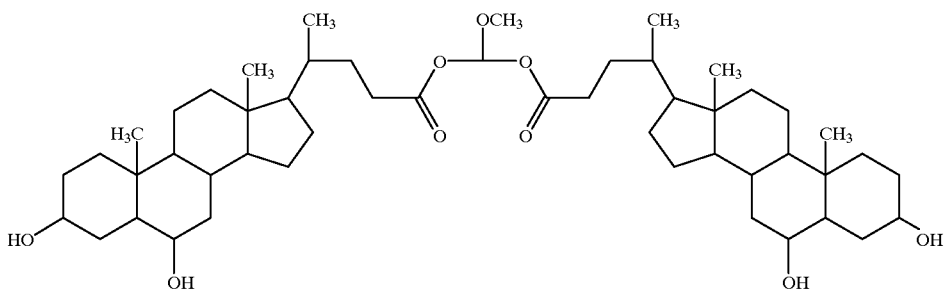

(X)

EXAMPLE 11

Carboxylic acid derivative was prepared in the same manner as Example 1 using cholic acid (71.1 g) instead of cyclohexane carboxylic acid (22.3 g), thus obtaining 60 g of the following compound (XI).

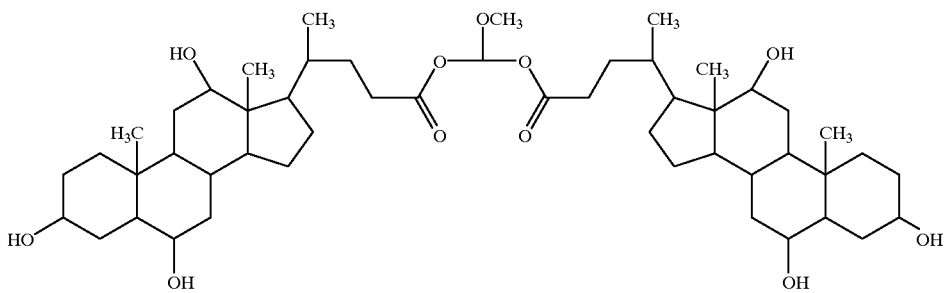

(XI)

EXAMPLE 12

Carboxylic acid derivative was prepared in the same manner as Example 1 using deoxycholic acid (68.3 g) instead of cyclohexane carboxylic acid (22.3 g) and α,α- dichloromethyl 2-norbomanemethyl ether (18 g) instead of α,α-dichloromethyl methyl ether (10 g), thus obtaining 59 g of the following compound (XII).

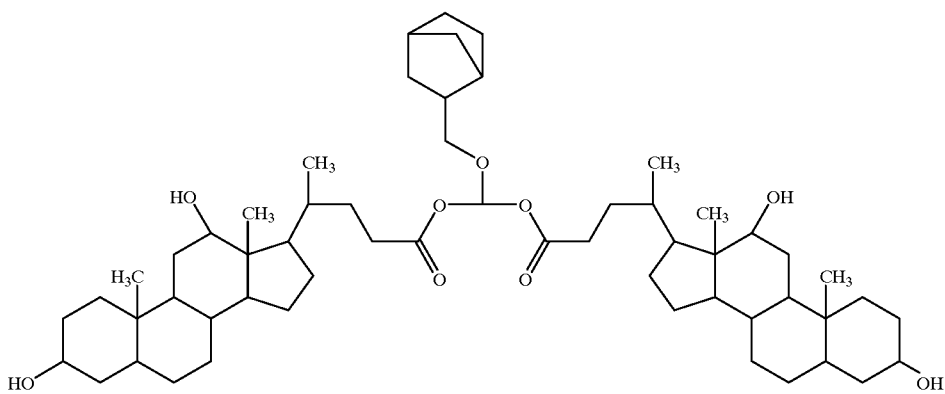

(XII)

EXAMPLE 13

Carboxylic acid derivative was prepared in the sarnemanner as Example 1 using deoxycholic acid (68.3 g) instead of cyclohexane carboxylic acid (22.3 g) and diiodomethane (23 g) instead of α,α-dichloromethyl methyl ether (10 g), thus obtaining 53 g of the following compound (XIII).

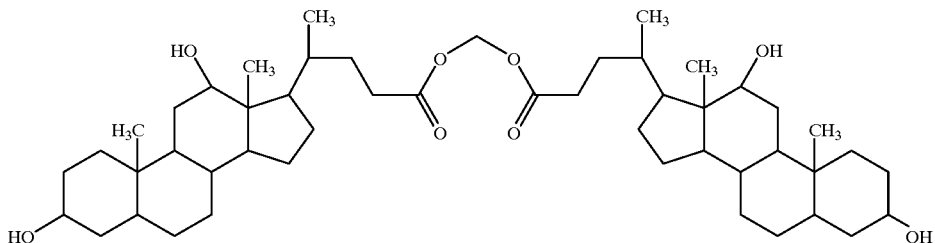

(XIII)

EXPERIMENTAL EXAMPLES 1 TO 2 AND COMPARATIVE EXPERIMENTAL EXAMPLES 1 TO 2

As shown in the following table 1, some components were dissolved and filtered by a 0.2 um membrane filter to obtain a resist solution. The remaining solution was coated on silicon wafer by rotation. The coated wafer was heated at 110° C. for 60 seconds. The wafers derived form Experimental example 1 and Comparative experimental example 1 was exposed by a ArF exposure system (ISI small field exposure system) and heated at 110° C. for 60 minutes. Then, the wafers were developed using an aqueous hydroxide solution for 60 minutes and dried to obtain a positive resist pattern.

Hence, the etching resistance is a relative figure based on i-line using.

According to Experimental example 2 and Comparative experimental example 2, the wafers were exposed by a Nikon KrF stepper.

TABLE 1

| Category | Composition | Resolution (um) | Etching resistance |
|---|---|---|---|
| Experimental example 1 | Resin 1: 20 g<br>Compound of Example 9: 4 g<br>Triphenylsulfonium trifluoromethane sulfonate: 0.36 g<br>Triethylamine: 0.018 g<br>Propyleneglycol monomethylether acetate: 140 g | 0.13 | 1.8 |
| Comparative Experimental example 1 | Resin 1: 24 g<br>Triphenylsulfonium trifluoromethane sulfonate: 0.36 g<br>Triethylamine: 0.018 g<br>Propylene glycol monomethylether acetate: 140 g | 0.15 | 2.3 |
| Experimental example 2 | Resin 2: 20 g<br>Compound of Example 9: 4 g<br>Triphenylsulfonium trifluoromethane sulfonate: 0.72 g<br>Triethylamine: 0.036 g<br>Propylene glycol monomethylether acetate: 120 g | 0.18 | 1.9 |

TABLE 1-continued

| Category | Composition | Resolution (um) | Etching resistance |
|---|---|---|---|
| Comparative Experimental example 2 | Resin 2: 24 g<br>Triphenylsulfonium trifluoromethane sulfonate: 0.72 g<br>Triethylamine: 0.036 g<br>Propylene glycol monomethylether acetate: 120 g | 0.20 | 2.4 |

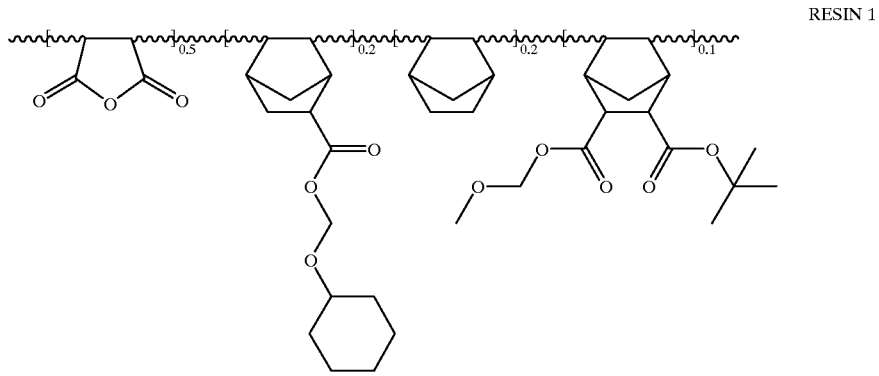

RESIN 1

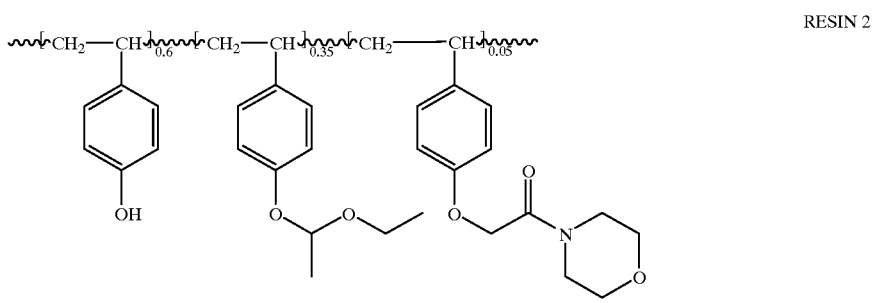

RESIN 2

As described above, the carboxylic acid derivatives of this invention, so prepared via condensation between carboxylic acid compound and halogen compounds, have several advantages in that (1) they are easily decomposed by acid but are not dissolved by basic aqueous solution, (2) more large monomolecular compound can be prepared. The carboxylic acid derivatives in a photoresist composition function not only as a dissolution inhibitor in the unexposed area to improve a dark erosion but also as a dissolution promoter in the exposed area due to formation of carboxylic acid, thus enhancement of pattern profile in a resist.

What is claimed is:

1. Carboxylic acid derivatives represented by the following formula I:

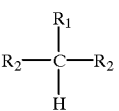

Formula I wherein $R_1$ is an hydrogen atom, an alkyl group or an alkoxy group of 1 to 20 carbon atoms in a linear, branched or cyclic form; $R_2$ is an alkylcarbonyloxy group wherein the alkyl group contains 1 to 40 carbon atoms in a linear, branched or cyclic form which is unsubstituted, or substituted with a hydroxy group, an ester group and an ether group.

2. Carboxylic acid derivatives according to claim 1, selected from the group consisting of the following compounds:

13
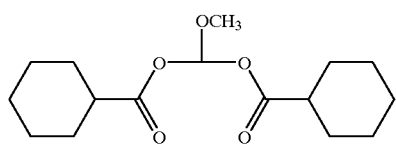
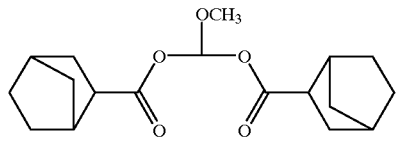
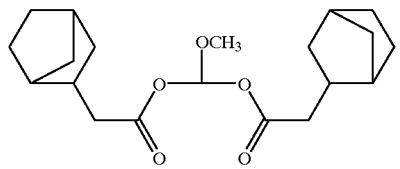
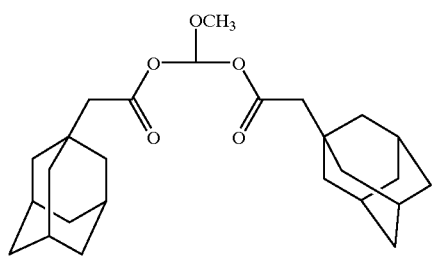
14
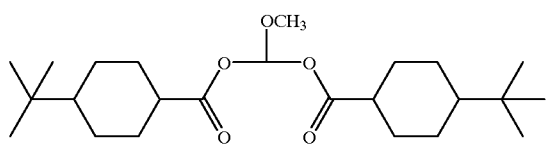
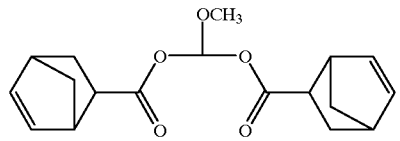
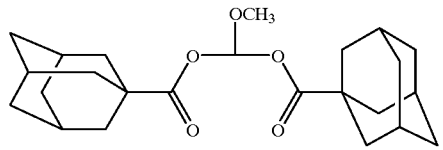
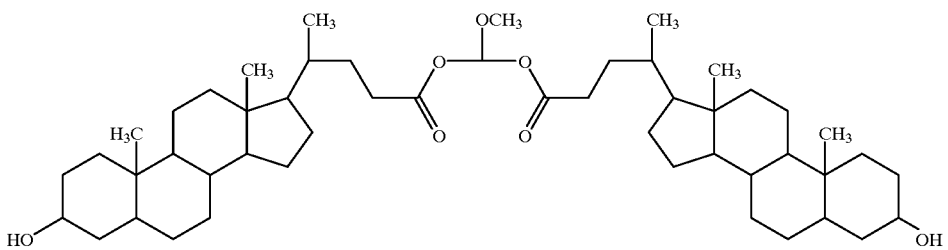
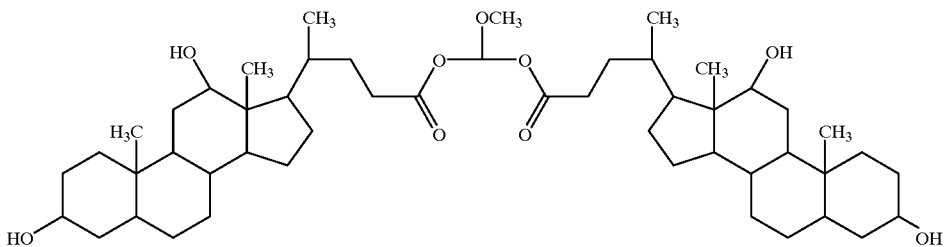
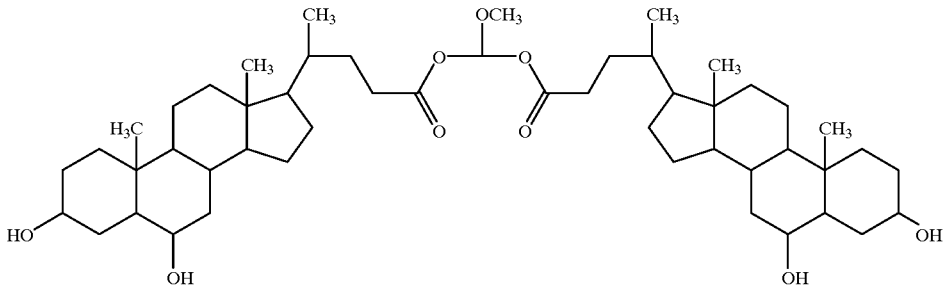

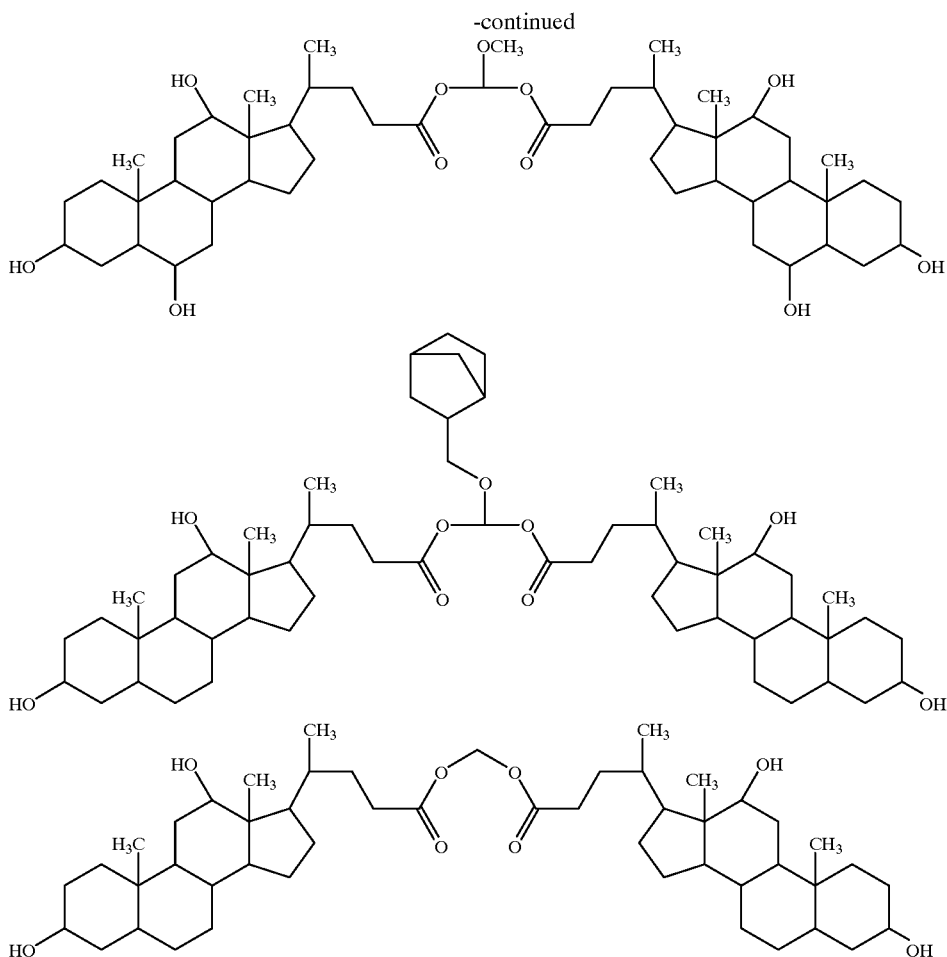

3. A method for synthesizing carboxylic acid derivatives represented by the formula I,

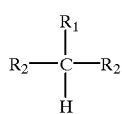

Formula I wherein one or more of the selected halogen compounds represented by the following formula II $R_1$—$CHX_2$ Formula II is/are reacted with one or more of the selected carboxylic acid compounds represented by the following formula III $R_2$—Formula III at −80 to −150° C. for 0.5 to 1.5 hours in the presence of a basic catalyst wherein $R_1$ is an hydrogen atom, an alkyl group or an alkoxy group of 1 to 20 carbon atoms in a linear, branched or cyclic form; X is F, Cl, Br or I; and $R_2$ is an alkylcarbonyloxy group wherein the alkyl group contains 1 to 40 carbon atoms in a linear, branched or cyclic form, which is unsubstituted, or substituted with a hydroxy group, an ester group and an ether group.

4. The method according to claim 3, wherein said basic catalyst is selected from the group consisting of amine, pyridines, organic metals, metals and mixture thereof.

5. method according to claim 3, wherein the carboxylic acid represented by formula III to the halogen compound represented by formula II is 1.5 to 3.0 equivalents.

* * * * *